United States Patent [19]
Guthrie et al.

[11] Patent Number: 5,619,992
[45] Date of Patent: Apr. 15, 1997

[54] METHODS AND APPARATUS FOR INHIBITING CONTAMINATION OF REUSABLE PULSE OXIMETRY SENSORS

[76] Inventors: Robert B. Guthrie, 1027 Church St., Ventura, Calif. 93001; Richard A. Potts, 7322 36th Ave. SW., Seattle, Wash. 98126

[21] Appl. No.: 417,975

[22] Filed: Apr. 6, 1995

[51] Int. Cl.⁶ .................................................. A61B 5/00
[52] U.S. Cl. ........................................ 128/633; 356/41
[58] Field of Search ................................ 128/633, 664, 128/665, 666, 667, 686, 715; 356/41; 206/305, 306

[56] References Cited

U.S. PATENT DOCUMENTS

| | | | |
|---|---|---|---|
| 3,295,675 | 1/1967 | Burns et al. | 206/63 |
| 3,650,153 | 3/1972 | Schwab | 73/343 |
| 3,833,115 | 9/1974 | Schapker | 206/306 |
| 4,197,944 | 4/1980 | Catlin | 206/306 |
| 4,359,052 | 11/1982 | Staub | 128/303 |
| 4,538,612 | 9/1985 | Patrick, Jr. | 128/333 |
| 4,548,249 | 10/1985 | Slaughterbeck | 128/686 |
| 4,593,699 | 6/1986 | Poncy et al. | 128/660 |
| 4,614,442 | 9/1986 | Poncy | 374/158 |
| 4,757,381 | 7/1988 | Cooper et al. | 600/121 |
| 4,846,344 | 7/1989 | Bala | 206/306 |
| 4,997,092 | 3/1991 | Dupont | 206/632 |
| 5,090,410 | 2/1992 | Saper et al. | 128/633 |
| 5,301,657 | 4/1994 | Lafferty | 128/6 |
| 5,363,843 | 11/1994 | Daneshvar | 128/630 |
| 5,413,101 | 5/1995 | Sugiura | 128/633 |
| 5,466,898 | 11/1995 | Gilbert et al. | 181/131 |
| 5,486,659 | 1/1996 | Rosenbush | 181/131 |

OTHER PUBLICATIONS

"Residual Bacterial Contamination on Reuable Pulse Nov. 1993, vol. 38, No. 11 Oximetry Sensors" by Martin C. Wilkins, Respiratory Care.

Primary Examiner—Angela D. Sykes
Assistant Examiner—Eric F. Winakur
Attorney, Agent, or Firm—Hughes, Multer and Schacht, P.S.

[57] ABSTRACT

A protective sheath for a pulse oximetry sensor. The sheath covers the sensor and inhibits contamination thereof during use. The sheath obviates the need to clean the pulse oximetry sensor after each use while reducing the likelihood of cross-patient contamination. The sheath allows the use of reusable pulse oximetry sensors and thus significantly reduces the overall costs of such sensors per use.

15 Claims, 6 Drawing Sheets

METHODS AND APPARATUS FOR INHIBITING CONTAMINATION OF REUSABLE PULSE OXIMETRY SENSORS

TECHNICAL FIELD

The present invention relates to pulse oximetry sensors and, more particularly, to covers for preventing contamination of such sensors.

BACKGROUND OF THE INVENTION

Continuous monitoring of arterial oxygen saturation by pulse oximetry ($S_aO_2$) has gained widespread use in health care. Pulse oximetry equipment comprises an infrared probe or sensor for generating a raw electrical signal from which arterial oxygen saturation may be calculated, a base unit for analyzing the raw electrical signal and displaying and recording arterial oxygen saturation, and a cable for connecting the probe or sensor to the base unit. The base unit and cable are well-known in the art and will not be described herein in detail.

Pulse oximetry sensors arrange an infrared source and an infrared detector on either side of a patient's digit such that an infrared light beam passes between the emitter and detector through the digit. Arterial oxygen saturation may be calculated from an electrical signal generated by the infrared detector.

Two basic types of pulse oximetry sensors are currently available: disposable and reusable. Disposable probes obviate the need to clean probes between each use, but are quite expensive given that they must be disposed after each use.

Reusable probes are relatively expensive to purchase at the outset but may be used many times, lowering the overall cost of probes for each use. However, reusable probes must be cleaned after each use, which inflates the actual cost of using reusable sensors; additionally, this cleaning process is fairly complex and increases the likelihood of cross-patient contamination if not performed carefully.

The present invention is of particular importance in the context of reusable pulse oximetry sensors, and that application will be described in detail herein. The present invention may have broader application, however, so the scope of the present invention should be determined not with reference to the following detailed description but instead with reference to the claims appended hereto.

OBJECTS OF THE INVENTION

From the foregoing, it should be clear that one primary object of the invention is to provide methods and devices for inhibiting contamination of pulse oximetry sensors.

Another more specific object of the present invention is to obtain methods and apparatus for inhibiting contamination of pulse oximetry sensors having a favorable mix of the following characteristics:

(a) allows the use of reusable pulse oximetry sensors;

(b) obviates the need to clean and sterilize reusable pulse oximetry sensors between each use;

(c) convenience of storage and use; and (d) ecologically sound; and (e) inexpensive to fabricate.

SUMMARY OF THE INVENTION

These and other objects are achieved by the present invention, which basically comprises a protective sheath that covers a reusable pulse oximetry sensor, but does not interfere with the operation of the pulse oximetry sensor. The sheath is made of a fluid-tight material, or substantially fluid-tight material in some cases, such as plastic film or the like. An opening is formed on at least one end of the sheath to allow the sensor to be inserted into an interior chamber of the envelope.

So that it does not interfere with the operation of the pulse oximetry sensor, the envelope interior chamber is provided with first and second chamber portions adapted to receive first and second sensor members. The sensor members are pivotally connected in a manner that allows them to engage and grip the patient's digit. The envelope is configured to have first and second sections thereof arranged between the patient's digit and the first and second sensor members. Aside from being fluid impermeable, the material from which the envelope is made should either be transparent so as not to interfere with the infrared light beam emitted and detected by the sensor, or to at least interfere therewith in a predictable manner that may be taken into account when the electrical signal generated by the sensor is processed.

Beyond this basic configuration, the protective sheath may be provided with skin-contacting material to prevent the skin from coming into direct contact with the fluid impermeable material from which the sheath is made. The skin-contacting material should be selected and configured to allow air to reach the patient's skin; the use of such skin-contacting material makes the process of measuring arterial oxygen saturation for long periods of time more comfortable.

Additionally, a second, sealable opening may be formed in the envelope to facilitate the insertion of the sensor into the sheath in the proper orientation.

The exemplary protective sheath disclosed herein optionally comprises a stiffening structure arranged about the opening in the envelope. This stiffening structure holds this opening in an open position to facilitate insertion of the sensor and cable attached thereto into the envelope. The stiffening structure may further comprise means for closing the structure about the cable and means for providing a fluid-tight seal at this opening about the cable.

To help improve the reliability of the present invention, the inside of the envelope may be coated with material that changes color when moistened to indicate the presence of contamination. Additionally, the interior of the envelope may be coated with an anti-bacterial substance or other substance designed to prevent contamination of the probe contained therein.

The protective sheath of the present invention substantially inhibits contamination of the pulse oximetry sensor and cable attached thereto, and in most cases will prevent this type of contamination. This allows the use of known reusable pulse oximetry sensors in a manner that obviates the need to clean these sensors thoroughly between each use. The cost of the disposable sheath of the present invention is substantially less than either the disposable probes or the process of cleaning reusable probes. The present invention can thus result in significant reduction in a facility's cost of continuously monitoring arterial oxygen saturation in its patients.

DETAILED DESCRIPTION OF THE INVENTION

Referring to FIGS. 1–4, the construction and use of a pulse oximetry sensor will initially be described to provide a thorough understanding of the environment in which the present invention will be used. Following that, the present invention will be described in detail with reference to FIGS. 5–15.

Figure 1:
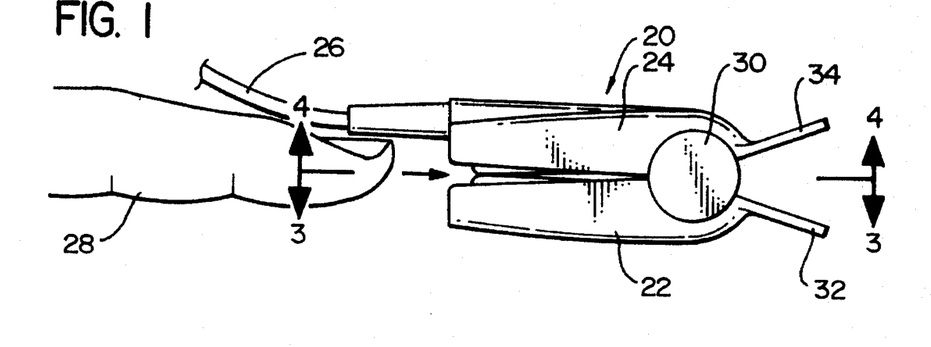
FIG. 1 is a side elevational view depicting a patient's digit being inserted into a reusable pulse oximetry sensor.
Figure 2:
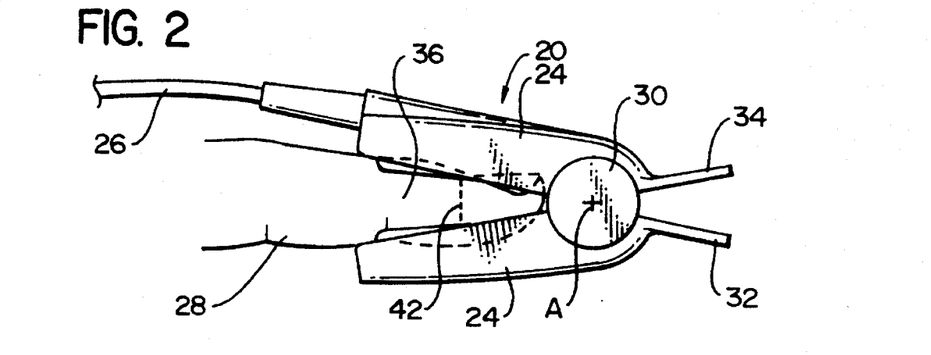
FIG. 2 depicts a side elevational view of a patient's digit received within a reusable pulse oximetry sensor.

A reusable pulse oximetry sensor 20 is shown in FIGS. 1 and 2. The pulse oximetry sensor 20 comprises a first sensor member 22 and a second sensor member 24 and is connected to a cable 26. As shown in FIG. 2, the sensor 20 is adapted to engage a patient's digit 28. The digit 28 may be the patient's finger as shown or, in other cases, another body member such as a toe, ear lobe, or the like.

Pulse oximetry sensors such as that shown at 20 in the Figures are generally well known and will be descried herein only briefly. The first and second sensor members are pivotally connected about a hinge pin 30 having a pivot axis A and are spring-biased into a closed position as shown in FIG. 1. The spring-bias may be overcome by pinching first and second handles 32 and 34 together to allow the sensor members 22 and 24 to be rotated into a clamping position as shown in FIG. 2.

A digit-receiving region 36 is defined between the sensor members 22 and 24. When the sensor is in its clamped position, the digit 28 is received in this digit-receiving region 36.

Figure 3:
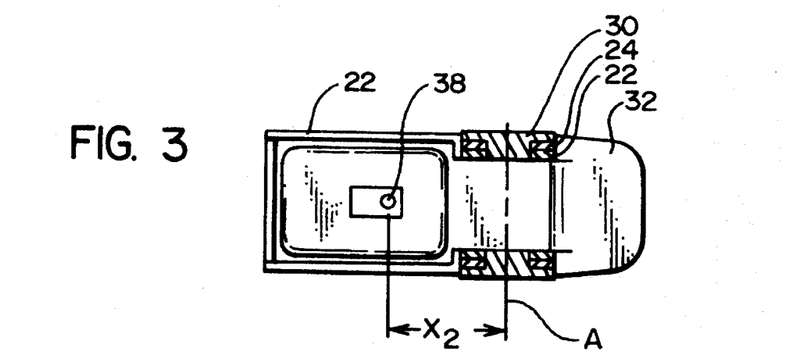
FIG. 3 is a bottom plan view taken along lines 3—3 in FIG. 1.
Figure 4:
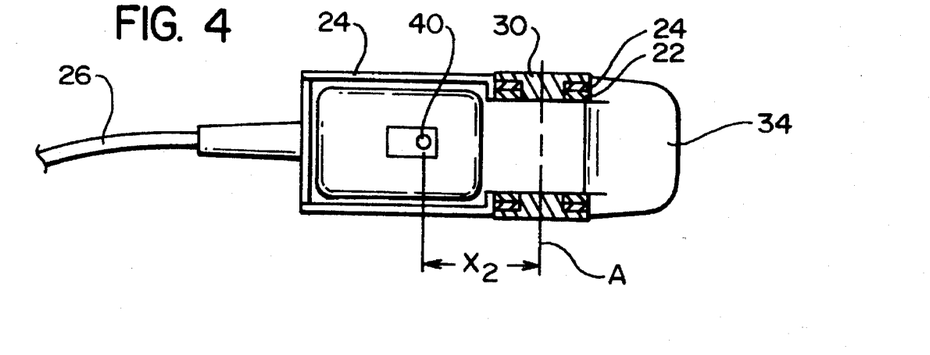
FIG. 4 is a top plan view taken along lines 4—4 in FIG. 1.

Turning now to FIGS. 3 and 4, it can be seen that an infrared emitter 38 is formed in the first sensor member 26, while an infrared detector 40 is formed in the second sensor member 24. Referring back for a moment to FIG. 2, an infrared light beam 42 can be seen which extends from the emitter 38 to the detector 40. The detector 40 generates an electrical signal from the light beam 42. Based on this electrical signal, a base unit (not shown in FIGS. 1–4) can determine arterial oxygen saturation of the patient.

Figure 5:
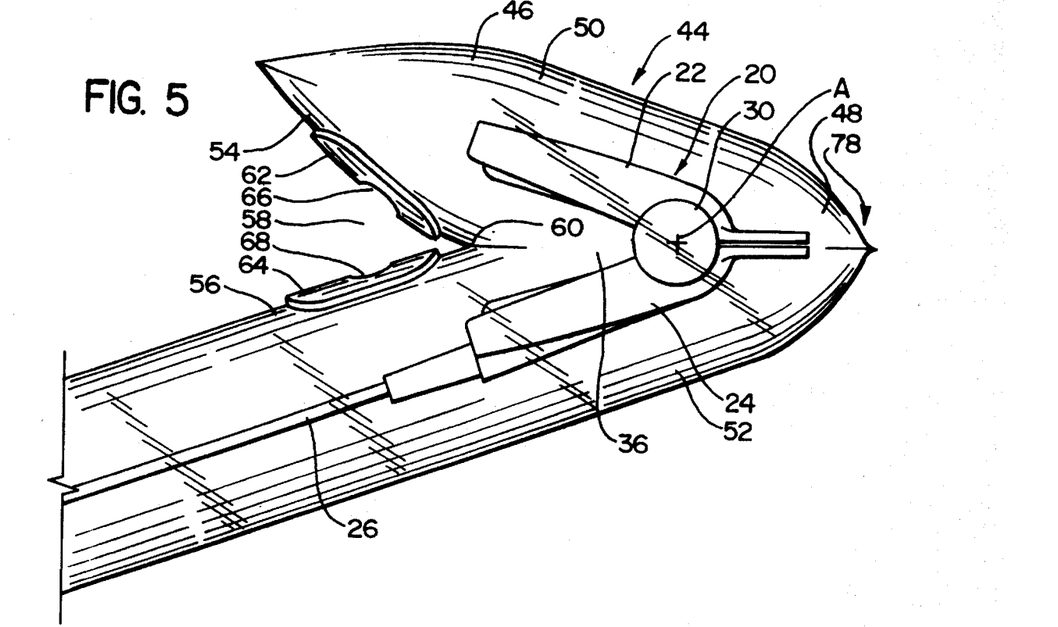
FIG. 5 is a partial side elevational view of a first embodiment of the present invention.
Figure 5A:
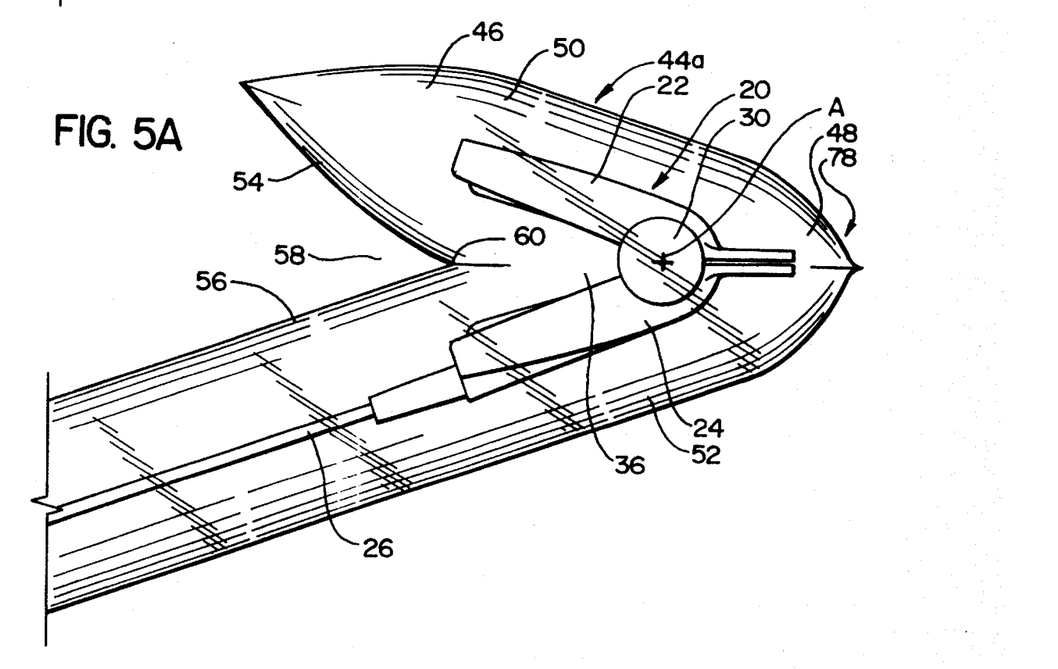
FIG. 5A is a partial side elevational view of a second embodiment of the present invention.

Referring now to FIGS. 5 and 5A, depicted at 44 and 44a therein are sheaths adapted to inhibit contamination of the sensor 20. Referring initially to FIG. 5, the sheath 44 comprises an envelope 46 of transparent, fluid-impermeable material. The envelope 46 defines an interior chamber 48 comprising a first cheer portion 50 and a second chamber portion 52.

As shown in FIG. 5, the first sensor member 22 is arranged in the first cheer portion 50, while the second member 24 is arranged in the second chamber portion 52.

The envelope 46 is configured such that a first section 54 thereof overlaps a second section 56 thereof; between these first and second sections 54 and 56 lies a notch region 58.

As will be described in further detail below, the sheath 44 and sensor 20 may be displaced relative to each other until the digit-receiving portion 46 defined by the sensor 20 is aligned with the notch region 58 defined by the envelope 46. When the digit-receiving region 36 is aligned with the notch region 58, a fold line 60 extending between the envelope first and second sections 54 and 56 is adjacent to, and parallel with, the pivot axis A of the hinge pin 30.

With the notch region 58 coextensive with the digit-receiving region 60 as just described, the envelope 46 does not hinder access to the digit-receiving region 36. Accordingly, the patient's digit may be placed into the digit-receiving region 36 and clamped by the sensor members 22 and 24 in exactly the same manner as that shown in FIG. 2.

Additionally, as the envelope 46 is made of substantially transparent material, the infrared light beam 42 may pass substantially unhindered from the first probe member 22 to the second probe member 24 through the first and second sections 54 and 56 of the envelope 46. But because the envelope 46 is fluid-impermeable, the sheath 44 presents a barrier to fluids and other materials to prevent these materials from contaminating the probe 20.

The difference between the envelopes 44 and 44a is that the envelope 44 further comprises first and second layers 62 and 64 of skin contacting material. In most situations, the sheath 44a would be appropriate. However, in certain circumstances, such as when it is necessary to measure arterial oxygen saturation for long periods of time, the sheath 44 may be preferable because the skin-contacting layer 62 and 64 are designed to allow the patient's skin to breath.

In particular, these layers 62 and 64 are formed of gauze or other material that allows air to reach the skin of the patient's digit 28. Thus, the skin-contacting layers 62 and 64, which are breathable, and not the envelope 46, which is not breathable, come into contact with the skin of the patient's digit 28. In some situations, it may be advisable to impregnate the skin-contacting layers 62 and 64 with an anti-microbial coating to inhibit microbial growth where the layers 62 and 64 contact the patient's digit 28.

Figure 7:
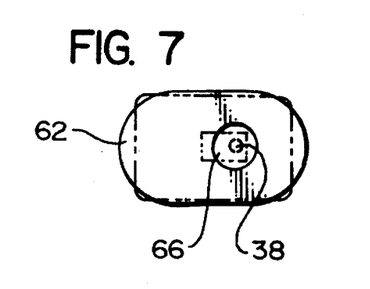
FIG. 7 depicts a configuration of digit receiving material used on the sheath depicted in FIG. 6.

Referring now to FIG. 7, that Figure shows that the layers 62 and 64 of skin-contacting material must be configured to allow the infrared light beam 42 to pass therethrough unobstructed. Accordingly, the layer 62 of skin-contacting material shown in FIG. 7 has a hole 66 formed therein. When the sheath 44 is arranged with the notch region 58 thereof aligned with the digit-receiving region 36, the infrared source 38 is visible through the hole 66, and the infrared light beam 42 may pass through the hole 66 and a similar hole 68 formed in the second layer 64 of digit-contacting material. The layers 62 and 64 of skin-contacting material thus provide additional comfort to the patient without adversely affecting the operation of the sensor 20.

Figure 6:
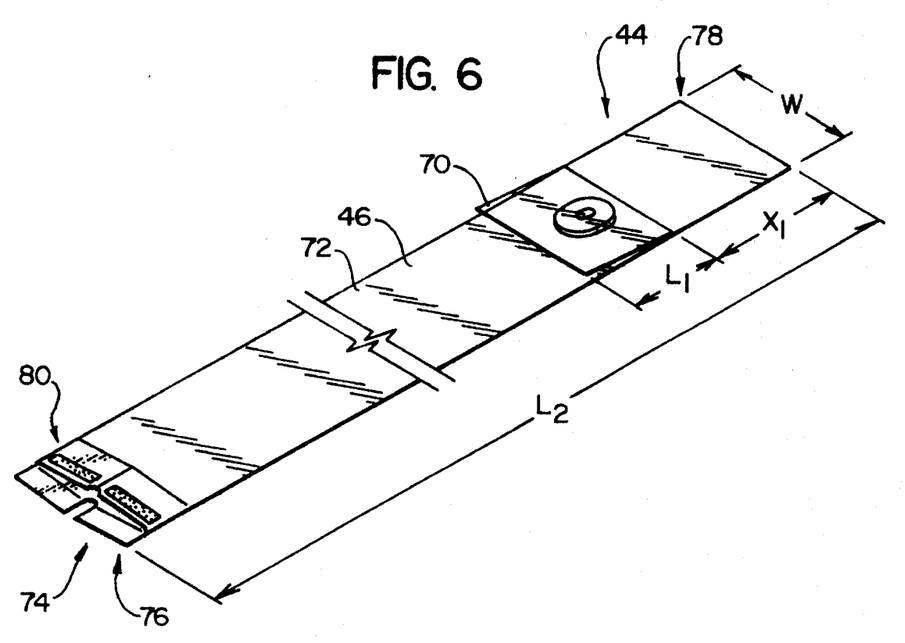
FIG. 6 depicts a perspective view of a protective sheath constructed in accordance with, and embodying, the principles of the present invention.

Referring now to FIG. 6, the sheath 44 is shown therein in its entirety. FIG. 6 shows that the envelope 46 comprises a first envelope portion 70 and a second envelope portion 72. Further, a cable opening 74 is formed at a first end 76 of the second envelope portion 72. The first envelope portion 70 is attached to the second envelope portion 72 adjacent to a second end 78 thereof. The first envelope portion 70 is the same width W as the second portion 72 but has a length $L_1$ is much shorter than a length $L_2$ of this second envelope portion 72. Additionally, the first envelope portion 70 is attached to the second envelope portion 72 a distance $X_1$ from the second portion second end 78. The distance $X_1$ is approximately the same as the distance $L_1$.

Referring again to FIGS. 3 and 4, it can be seen that the emitter 38 and detector 40 are arranged a distance $X_2$ from the hinge axis A. Similarly, with reference to FIG. 5, centers of the holes 66 and 68 are located a distance $X_3$ from the fold line 60. These distances $X_2$ and $X_3$ are approximately the same so that when the fold line 60 is adjacent to the axis A of the hinge member 30, the holes 66 and 68 are aligned with the emitter 38 and detector 40, respectively.

The following Table A sets forth the exemplary lengths associated with the variables described above along with first and second preferred ranges for these variables. All measurements are in inches.

TABLE A

| Variable | Exemp. Embod. | First Preferred Range | | Second Preferred Range | |
|---|---|---|---|---|---|
| | | Min. | Max. | Min. | Max. |
| W | 2.0 | 1.75 | 2.50 | 1.5 | 3.0 |
| $L_1$ | 21 | 13 | 31 | 8 | 68 |
| $L_2$ | 24 | 18 | 36 | 12 | 72 |
| $X_1$ | 3.0 | 2.25 | 3.50 | 2 | 5 |
| $X_2$ | 1.0 | 0.75 | 1.5 | 0.5 | 2 |
| $X_3$ | 0.50 | 0.3750 | 0.75 | 0.25 | 1 |

FIG. 6 also depicts a stiffening structure 80 mounted on the first end 76 of the second envelope portion 72. The basic purpose of this stiffening structure 80 is to hold the cable opening 74 open for the insertion of the sensor 20. A second purpose of this stiffening structure 80 is to allow the cable opening 74 to be closed.

Figures 8, 9, 10, 11:
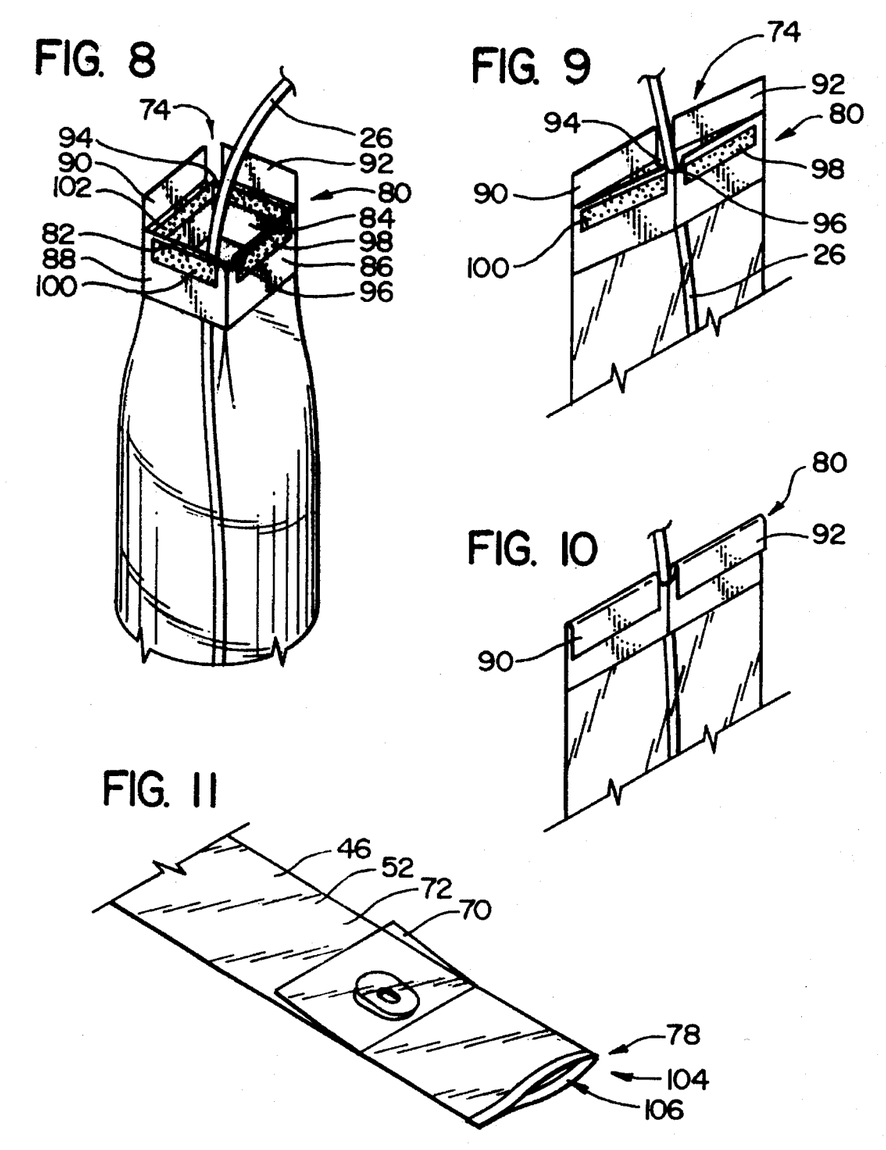
FIGS. 8, 9, and 10 depict the structure and use of a stiffening member of the protective sheath shown in FIG. 6.
FIG. 11 depicts another exemplary protective sheath constructed in the same basic manner as that shown in FIG. 6, but having two openings formed therein.

In particular, FIG. 8 shows that the stiffening structure 80 may be placed in a distended position in which the cable opening 74 is in a wide open position. FIG. 9 shows the stiffening structure 80 in a flattened position. FIG. 10 shows the sniffening structure 80 in a sealed position. The stiffening structure may be a paperboard or plastic structure formed separately from and attached to the sheath 44 or may be integrally formed with the sheath 44 as will be described below with reference to FIG. 16.

The exemplary stiffening structure 80 is formed of a box having first, second, third, and fourth sides 82, 84, 86, and 88. First and second flaps 90 and 92 are formed on the first and second sides 82 and 84. Notches 94 and 96 are formed at the junctures of the upper edges of the sides 82 and 84 and on the sides 86 and 88, respectively. Additionally, adhesive strips 98 and 100 are formed on the outer surfaces of the third and fourth sides 86 and 88.

When the stiffening structure 80 is in its flattened position, the cable 26 is arranged adjacent to the notches 94 and 96 and the flaps 90 and 92 are folded over to engage the adhesive strips 100 and 98 as shown in FIG. 10.

Additionally, to inhibit fluid flow through the cable opening when the stiffening structure 80 is in the sealed position as shown in FIG. 10, a continuous strip 102 (FIG. 8) of flexible material may be formed around the interior surfaces of the sides 82, 84, 86, and 88. When the stiffening member 80 is in the sealed position shown in FIG. 10, the resilient strip 102 will engage itself and the cable 26 to help prevent fluid passage into the interior chamber 48. This strip 102 will also engage the cable 26 to inhibit relative movement between the cable 26 stiffening structure 80.

A number of modifications to the sheath 44 shown in FIGS. 5 and 6–10 improve the operation thereof under certain circumstances. Referring initially to FIG. 11, it can be seen that an optional insertion opening 104 may be formed in the envelope 46. In particular, this insertion opening 104 is formed in the second end 78 of the second envelope portion 72. A sealing structure 106 is formed at the insertion opening 104 to allow opening 104 to be closed in a fluid-tight manner. The sealing structure 106 may be a tongue-in-groove type locking fastener such as that found on plastic bags such as resealable sandwich bags and permanently sealable plastic banking bags.

In use, an end of the cable distal from the sensor 20 may be dropped into the insertion opening and fed through the second cheer portion 52 until the distal end of the cable passes through the cable opening 74 and the sensor 20 enters the interior chamber 48.

Referring now to FIGS. 12–15, a second type of reusable sensor 120 is depicted therein. The sensor 120 operates in the same basic manner as the sensor 20 described above. However, instead of having its first and second probe members 122 and 124 pivotally connected together, these members are flexible and extend out from a body portion 130. The first and second sensor members 122 and 124 are arranged on opposite sides of a digit 128 such that an infrared light beam emitted from an emitter 132 passes through the digit 128 before being detected by the detector 134.

Figure 12:
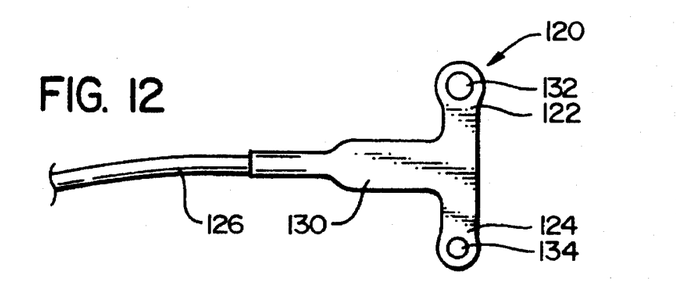
FIG 12 depicts a side elevational of a second type of pulse oximetry sensor.
Figure 13:
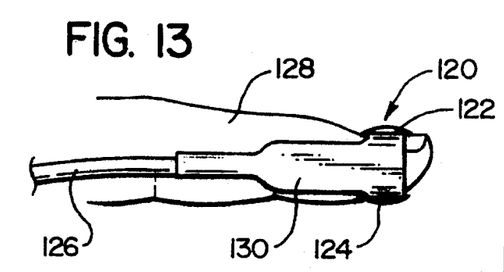
FIG. 13 depicts a view of the sensor shown in FIG. 12 in use.
Figure 14:
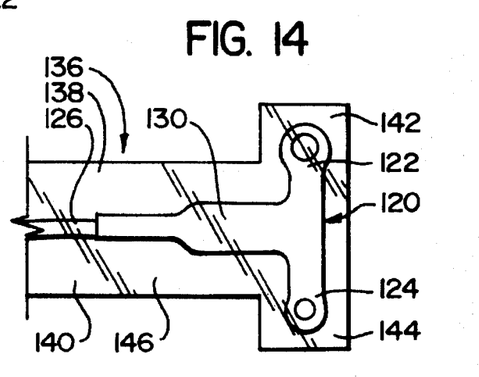
FIG. 14 depicts a side elevational view of a protective sheath constructed in accordance with the present invention adapted to inhibit contamination of a probe such as that shown in FIG. 12.

With a sensor 120 as shown in FIGS. 12 and 13, a protective sheath 136 comprises an envelope 138 defining an inner cheer 140. The inner chamber 140 comprises a first portion 142, a second portion 144, and a third portion 146. The first probe member 122 is received in the first chamber portion 142, while the second sensor member 124 is received by the second chamber portion 144. The main body portion 130 and cable 126 are received by the third chamber portion 146. Again, the envelope 138 is made of transparent, fluid-impermeable material.

Figure 15:
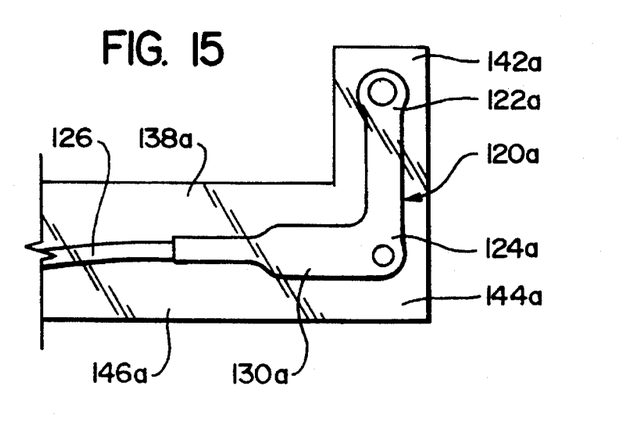
FIG. 15 depicts a side elevational view of yet another protective sheath constructed in accordance with the present invention and adapted to inhibit contamination of a probe similar to that shown in FIG. 12.

Referring now to FIG. 15, depicted therein at 120a is a sensor in which the first sensor member 122a, second sensor member 124a, and third main portion 130a are arranged in a generally L-shaped configuration. In this case, the envelope 138a defines first, second, and third chamber portions 142a, 144a, and 146a in a similar L-shaped configuration.

Figure 16:
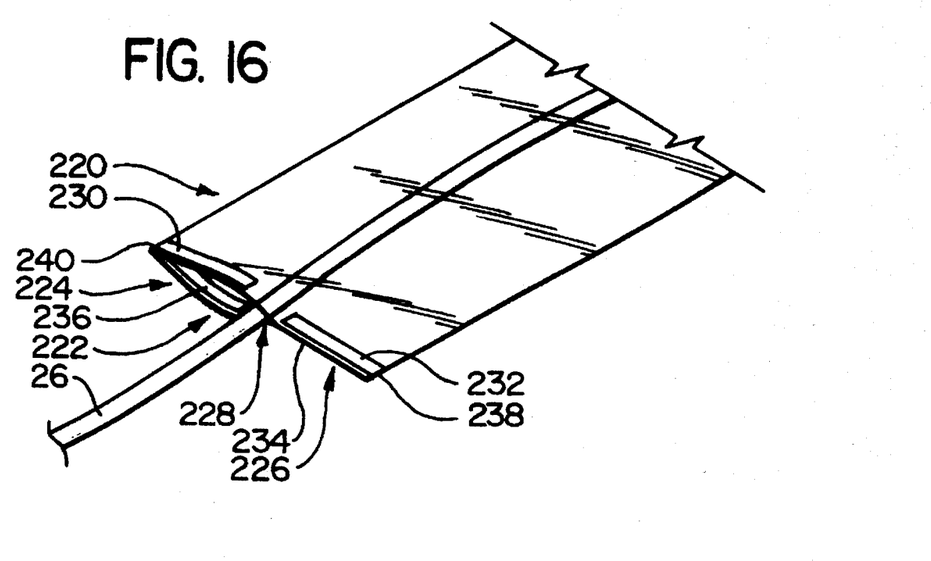
FIG. 16 depicts a perspective view of a closure means that may be employed to close a cable opening.
Figure 17:
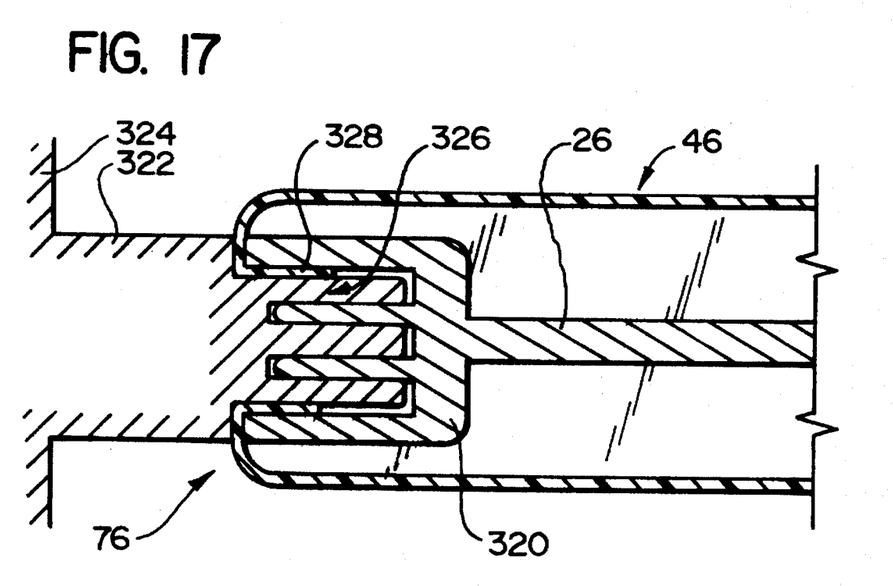
FIG. 17 depicts the interaction of a base unit, connector, and protective sheath that will form a closure and sealing means around the cable.

Referring now to FIGS. 16 and 17, these Figures show additional means for closing the cable opening 74. The means for closing the cable opening 74 shown in FIG. 16 also forms an integral stiffening structure that functions in a manner similar to that shown in FIGS. 6 and 8–10.

In particular, in FIG. 16, another exemplary protective sheath 220 having a cable opening 222 is shown. Two tongue-in-groove fasteners 224 and 226 are arranged adjacent to the cable opening 222, with a cable channel 228 extending between these fasteners 224 and 226.

The fasteners 224 and 226 form an integral stiffening structure having four separate segments 230, 232, 234, and 236 that function in a manner basically similar to the four sides 82, 84, 86, and 88 of the stiffening 80 described above. By pinching the sheath 220 between fingers at a first location 238 between the segments 232 and 234 and a second location 240 between the segments 236 and 230, the cable opening 220 may be placed in an open position similar to that shown in FIG. 8. The sensor may then be inserted through the opening 220 as discussed above.

The cable 26 is then aligned with the cable channel 228, and the fasteners 224 and 226 are engaged to close the cable opening 222. The cable opening 222 is not seal by this arrangement, but this arrangement will substantially inhibit passage of fluids to the interior of the sheath 220.

Also, friction between the sheath material and the cable 26 will tend to inhibit the sliding of the sheath along the cable 26. This friction can be enhanced, and a better seal will be formed, by placing a strip of resilient material along the inside of the cable opening 222 similar to the resilient strip 102 described above.

Referring now to FIG. 17, this Figure shows a modification to the protective sheath 46 having an insertion opening 104 closeable using a sealing structure 106 as shown in FIG. 11. With an insertion opening 104 as shown in FIG. 11, there is no need to form a cable opening in the sheath 46; thus, the modification to the sheath 46 as shown in FIG. 17 comprises forming the sheath 46 with a completely closed first end 76. A connector 320 formed on the end of the cable 26 is contained within this closed first end 76.

To allow this connector 320 to mate with a connector 322 on the base unit 324, the connectors 320 and 322 are simply forced together in a similar manner with the sheath 46 in between. The connectors 320 and 322 will pierce the sheath 46 to form a connector opening 326 therein.

Additionally, a portion 328 of the sheath 46 adjacent to the first end 76 will be gripped between the connectors 320 and 322. This gripping action will fix the first end 76 of the cable 26 in place relative to the sheath 46 and will form a seal around the connector opening 326 that will substantially inhibit fluid flow therethrough.

The above mentioned sheaths are used in one of two basic methods. First, if the sheath has a cable opening and no insertion opening, the sensor 20 is fed through the cable opening at the first end of the sheath until the sensor is within the sheath adjacent to the second end thereof. The use of a stiffening member can help insertion of the sensor through the cable opening.

The sensor is then manipulated such that the sensor members are in their respective chamber portions. With the sensor 20, the handles 32 and 34 thereof are pinched together to separate the sensor members 22 and 24 during the step of manipulating the sensor members into their respective chamber portions.

The cable opening may then be closed with a clip, stiffening structure, or integral fastener to inhibit passage of fluid through this opening and prevent the sheath from riding up the cable.

The sensor is then used in its normal manner as described with reference to FIGS. 1–4.

A second basic method is used when an insertion opening is formed in the second end of the sheath. In this case, the cable is first fed through the insertion opening until the cable connector reaches the second end of the sheath. The sensor is then manipulated as in the first method to place the sensor members in their respective chamber portions. The insertion opening is then sealed.

If the sheath is provided with a cable opening, the cable connector is passed through this opening so that it may be plugged into a base unit. The first end of the sheath member is then closed using a clip, integral fastener, or an adhesive stiffening structure to inhibit passage of fluid therethrough and prevent the sheath from riding up the cable towards the sensor.

If the sheath does not have a cable opening as shown in FIG. 17, the cable connector is grasped and inserted into the base connector in a normal manner, except that the connectors interact to pierce the sheath as they mate.

The sensor member is then placed over a patient's digit as described above and used in a conventional manner.

After either of these two basic methods, the sheath is disposed.

It should be clear from the foregoing that the present invention may be embodied in other specific forms without departing from the essential characteristics thereof. The present embodiments are therefore to be considered in all respects as illustrative and not restrictive, the scope of the invention being indicated by the appended claims rather than by the foregoing description; all changes which come within the meaning and range of equivalency of the claims are therefore intended to be embraced therein.

I claim:

1. A method of inhibiting contamination of a pulse oximetry sensor having first and second sensor members and a sensor cable, comprising the steps of:

providing an envelope of fluid impermeable material, the envelope having an interior chamber comprising a first chamber portion and a second chamber portion and having a first envelope section adjacent to the first chamber portion and a second envelope section adjacent to the second chamber portion;

forming an insertion opening in the envelope;

forming a cable opening in the envelope;

passing the cable through the insertion opening and the cable opening until the first and second sensor members are within the interior chamber;

manipulating the oximetry sensor such that the first sensor member is in the first chamber portion and the second sensor member is in the second chamber portion;

sealing the insertion opening; and placing a patient's digit into a notch region at least partially defined by the first and second envelope sections such that a beam of light may pass between the first and second sensor members through the patient's digit.

2. A combination of:

a pulse oximetry sensor comprising a cable and a sensor assembly formed by first and second sensor members mounted to the end of the cable, the sensor members being pivotally connected to move between a closed position and an open position in which a digit receiving region is defined therebetween;

a protective sheath comprising an envelope having an interior chamber comprising a first chamber portion and a second chamber portion and having a cable opening formed therein to allow access to the interior chamber, the envelope being made of fluid impermeable material and having a first envelope section adjacent to the first chamber portion and a second envelope section adjacent to the second chamber portion; wherein the protective sheath is placed over the pulse oximetry sensor such that the first sensor member is received in the first chamber portion, the second sensor member is received in the second chamber portion, and the cable extends through the cable opening; and the first and second envelope sections are adjacent to the first and second sensor members, respectively, such that access to the digit receiving region is substantially unhindered.

3. A protective sheath for inhibiting contamination of a pulse oximetry sensor having first and second sensor members adapted to engage a patient's digit, the protective sheath comprising:

an envelope having an interior chamber comprising a first chamber portion and a second chamber portion and having a cable opening formed therein to allow access to the interior chamber, the envelope being made of fluid impermeable material; wherein the pulse oximetry sensor is received within the interior chamber such that the first sensor member is received in the first chamber portion and the second sensor member is received in the second chamber portion;

with the pulse oximetry sensor so received within the interior chamber, the envelope defines a notch region partly bounded by first and second sections of the envelope that are adjacent to the first and second sensor members, respectively;

the envelope comprises a first envelope portion defining the first chamber portion and a second envelope portion defining the second chamber portion, where the cable opening is formed in a first end of the second envelope portion and the first envelope portion is adjacent to a second end of the second envelope portion;

the protective sheath further comprising first and second layers of skin contacting material attached to the first and second portions of the envelope, where the skin contacting layers are formed from a breathable material that allows air to reach the patient's digit.

4. A protective sheath as recited in claim 3, in which the first and second layers of skin contacting material are configured to allow a beam of light to pass from the first sensor member to the second sensor member substantially unobstructed.

5. A protective sheath for inhibiting contamination of a pulse oximetry sensor having first and second sensor members adapted to engage a patient's digit, the protective sheath comprising:

an envelope having an interior chamber comprising a first chamber portion and a second chamber portion and having a cable opening formed therein to allow access to the interior chamber, the envelope being made of fluid impermeable material; wherein the pulse oximetry sensor is received within the interior chamber such that the first sensor member is received in the first chamber portion and the second sensor member is received in the second chamber portion;

with the pulse oximetry sensor so received within the interior chamber, the envelope defines a notch region partly bounded by first and second sections of the envelope that are adjacent to the first and second sensor members, respectively;

an insertion opening is formed in the envelope to allow access to the interior chamber;

the protective sheath further comprising means for closing the insertion opening to inhibit entry of fluids into the interior chamber through the insertion opening.

6. A protective sheath for inhibiting contamination of a pulse oximetry sensor having first and second sensor members adapted to engage a patient's digit, the protective sheath comprising:

an envelope having an interior chamber comprising a first chamber portion and a second chamber portion and having a cable opening formed therein to allow access to the interior chamber, the envelope being made of fluid impermeable material; wherein the pulse oximetry sensor is received within the interior chamber such that the first sensor member is received in the first chamber portion and the second sensor member is received in the second chamber portion;

with the pulse oximetry sensor so received within the interior chamber, the envelope defines a notch region partly bounded by first and second sections of the envelope that are adjacent to the first and second sensor members, respectively;

the protective sheath further comprising stiffening means mounted to the envelope at the cable opening to allow the cable opening to be held in a wide open position.

7. A protective sheath as recited in claim 6, in which the stiffening means comprises a semi-rigid structure movable between a distended position and a flattened position, in which the cable opening is in the wide open position when the semi-rigid structure is in its distended position.

8. A protective sheath as recited in claim 7, further comprising attachment means for holding the semi-rigid structure in its flattened position.

9. A protective sheath as recited in claim 7, in which the semi-rigid structure is made of a material chosen from the group of paperboard and plastic.

10. A protective sheath as recited in claim 7, further comprising sealing means mounted to the interior of the semi-rigid structure.

11. A method of inhibiting contamination of a pulse oximetry sensor having first and second sensor members and a sensor cable, comprising the steps of:

providing an envelope of fluid impermeable material, the envelope having an interior chamber comprising a first chamber portion and a second chamber portion;

forming a cable opening in the envelope;

passing the first and second sensor members through the cable opening;

manipulating the oximetry sensor such that the first sensor member is in the first chamber portion, the second sensor member is in the second chamber portion, and the cable extends through the cable opening;

attaching first and second layers of skin contacting material to the first and second sections of the envelope; and placing a patient's digit into a notch region at least partially defined by first and second sections of the envelope such that a beam of light may pass between the first and second sensor members through the patient's digit; wherein air may reach portions of the patient's digit in contact with the skin contacting material.

12. A method as recited in claim 11, further comprising the step of configuring the first and second layers of skin contacting material to allow a beam of light to pass from the first sensor member to the second sensor member substantially unobstructed.

13. A method of inhibiting contamination of a pulse oximetry sensor having first and second sensor members and a sensor cable, comprising the steps of:

providing an envelope of fluid impermeable material, the envelope having an interior chamber comprising a first chamber portion and a second chamber portion;

forming a cable opening in the envelope;

passing the first and second sensor members through the cable opening;

manipulating the oximetry sensor such that the first sensor member is in the first chamber portion, the second sensor member is in the second chamber portion, and the cable extends through the cable opening;

placing a patient's digit into a notch region at least partially defined by first and second sections of the envelope such that a beam of light may pass between the first and second sensor members through the patient's digit;

providing a stiffening structure at the cable opening; and holding the stiffening structure in an open position to place the cable opening in a wide open position before the step of passing the first and second sensor members through the cable opening.

14. A method as recited in claim 13, further comprising the steps of adhering the semi-rigid structure in a flattened position after the step of passing the first and second sensor members through the cable opening.

15. A method of inhibiting contamination of a pulse oximetry sensor having first and second sensor members and a sensor cable, comprising the steps of:

providing an envelope of fluid impermeable material, the envelope having an interior chamber comprising a first chamber portion and a second chamber portion;

forming a cable opening in the envelope;

passing the first and second sensor members through the cable opening;

manipulating the oximetry sensor such that the first sensor member is in the first chamber portion, the second sensor member is in the second chamber portion, and the cable extends through the cable opening;

placing a patient's digit into a notch region at least partially defined by first and second sections of the envelope such that a beam of light may pass between the first and second sensor members through the patient's digit; and substantially sealing the cable opening after the step of passing the first and second sensor members through the cable opening.

* * * * *